US010935542B2

(12) United States Patent
O'Connor et al.

(10) Patent No.: US 10,935,542 B2
(45) Date of Patent: Mar. 2, 2021

(54) METHOD FOR IDENTIFICATION AND CULTURE OF MULTIPOTENT MESENCHYMAL STEM CELLS WITH HIGH PROLIFERATION POTENTIAL

(75) Inventors: Kim O'Connor, New Orleans, LA (US); Katie Russell, New Orleans, LA (US)

(73) Assignee: THE ADMINISTRATORS OF THE TULANE EDUCATIONAL FUND OFFICE OF TECHNOLOGY TRANSFER AND INTELLECTUAL PROPERTY DEVELOPMENT, New Orleans, LA (US)

( * ) Notice: Subject to any disclaimer, the term of this patent is extended or adjusted under 35 U.S.C. 154(b) by 815 days.

(21) Appl. No.: 13/992,953

(22) PCT Filed: Dec. 21, 2011

(86) PCT No.: PCT/US2011/066385
§ 371 (c)(1),
(2), (4) Date: Jun. 10, 2013

(87) PCT Pub. No.: WO2012/088225
PCT Pub. Date: Jun. 28, 2012

(65) Prior Publication Data
US 2013/0273570 A1    Oct. 17, 2013

Related U.S. Application Data

(60) Provisional application No. 61/459,987, filed on Dec. 22, 2012.

(51) Int. Cl.
*G01N 33/50* (2006.01)
*C12N 5/0775* (2010.01)

(52) U.S. Cl.
CPC ....... *G01N 33/5073* (2013.01); *C12N 5/0662* (2013.01); *C12N 5/0663* (2013.01);
(Continued)

(58) Field of Classification Search
None
See application file for complete search history.

(56) References Cited

U.S. PATENT DOCUMENTS

2007/0128722 A1\* 6/2007 Lin ...................... C12N 5/0663
435/366
2009/0274663 A1\* 11/2009 Shiels .................. C12N 5/0607
424/93.7

FOREIGN PATENT DOCUMENTS

| EP | 2186883 | 5/2010 |
| WO | WO2011141789 | 11/2011 |
| WO | PCT/US2011/066385 | 12/2011 |

OTHER PUBLICATIONS

Crisan et al, A Perivascular Origin for Mesenchymal Stem Cells in Multiple Human Organs, 2008, Cell Stem Cell, 3:301-313.\*
(Continued)

*Primary Examiner* — Sharmila G Landau
*Assistant Examiner* — Stephanie A McNeil
(74) *Attorney, Agent, or Firm* — Boulware & Valoir

(57) ABSTRACT

Variations in the differentiation and lineage potential of stem cells, including mesenchymal stem cells, currently limit their therapeutic use. The ability to identify, isolate, and specifically amplify stem cell populations with desired differentiation potential would contribute the use of stem cells in research and therapy. The present invention discloses a method of assessing differentiation potential of stem cells by measuring the differential expression of antigens CD146 and NG2 on the stem cells. The correlation between CD146 and NG2 expression and differentiation and trilineage potential is explored. The invention also discloses methods to
(Continued)

specifically amplify or enrich stem cells with desired differentiation potential, monitor the differentiation potential of a heterogeneous stem cell population, quantify the heterogeneity in differentiation potential of a stem cell culture, and remove stem cells with specific differentiation potentials from a heterogeneous cell culture.

16 Claims, 7 Drawing Sheets

(52) U.S. Cl.
CPC . *G01N 33/5005* (2013.01); *G01N 2333/4722* (2013.01); *G01N 2333/70596* (2013.01)

(56) References Cited

OTHER PUBLICATIONS

Hoogduijn et al, Comparative Characterization of Hair Follicle Dermal Stem Cells and Bone Marrow Mesenchymal Stem Cells, 2006, Stem Cells and Development, 15(1): 49-60.*

Da Silva Meirelles et al, In Search of the In Vivo Identity of Mesenchymal Stem Cells, 2008, Stem Cells, 26(9):2287-99.*

Kozanoglu et al, Human bone marrow mesenchymal cells express NG2: possible increase in discriminative ability of fl ow cytometry during mesenchymal stromal cell identifi cation 2009, Cytotherapy, 11(5): 527-533.*

Stallcup et al, The NG2 proteoglycan: Past insights and future prospects, 2002, Journal of Neurocytology, 31: 423-435.*

Russel et al., "In vitro high-capacity assay to quantify the clonal heterogeneity in trilineage potential of mesenchymal stem cells reveals a complex hierarchy of lineage commitment" Stem Cells, vol. 28, pp. 788-798 (Feb. 1, 2010).

Tsai et al., 'The mood stabilizers valproic acid and lithium enhance mesenchymal stem cell migration via distinct mechanisms' Neuropsychopharmacology, vol. 35, pp. 2225-2237 (Jul. 7, 2010).

KOzanoglu Ilknur et al: "Human bone marrow mesenchymal cells express NG2: possible increase in discriminative ability of flow cytometry during mesenchymal stromal cell identification", Cytotherapy, Elsevier, England, vol. 11, No. 5, Jan. 1, 2009, pp. 527-533.

Sorrentino A. et al.: Isolation and characterization of CD146+ multipotent mesenchymal stromal cells:, Experimental Hematology, Elsevier, Inc., US, vol. 36, No. 8, Aug. 1, 2008, pp. 1035-1046.

* cited by examiner

METHOD FOR IDENTIFICATION AND CULTURE OF MULTIPOTENT MESENCHYMAL STEM CELLS WITH HIGH PROLIFERATION POTENTIAL

CROSS-REFERENCE TO RELATED APPLICATIONS

This application claims priority under 35 U.S.C. Sec. 119(e) to U.S. Provisional Application 61/459,987, filed Dec. 22, 2010, which is incorporated by reference in its entirety. This application also claims priority to PCT application No. PCT/US2011/066385, filed Dec. 21, 2011, which is also incorporated by reference in its entirety.

STATEMENT REGARDING FEDERALLY SPONSORED RESEARCH

This invention was made with government support under Grant Number NIH-R03EB007281 awarded by the National Institutes of Health, and Grant Numbers NSF-BES0514242 and NSF-CBET1066167 awarded by the National Science Foundation. The government has certain rights in the invention.

FIELD OF THE INVENTION

The present invention relates to identification and isolation of Mesenchymal stem cells (MSCs) that are multipotent and highly efficient in colony formation using immunophenotyping.

BACKGROUND OF THE INVENTION

Mesenchymal stem cells (MSCs) are a promising type of adult stem cells for regenerative therapies. A major challenge to realizing the therapeutic potential of MSCs is variation in their progenitor content of MSC cultures which are a heterogeneous mixture of differentiated cells and undifferentiated progenitors of various potencies (or differentiation potentials). Multipotent MSCs exhibit a broad range of regenerative properties that include differentiation into mesenchymal lineages, rapid cell proliferation and secretion of trophic factors. MSC therapies are being developed to repair damage to mesenchymal and non-mesenchymal tissues. The efficacy of these treatments is strongly affected by variation in progenitor content from different donors and upon ex vivo expansion. Control of progenitor content is hindered by the absence of an immunophenotype to identify multipotent MSCs in heterogeneous cultures. The use of specific cell-surface markers of MSC multipotency and high efficiency colony formation potentials is useful in isolating and identifying MSCs with therapeutic potential. There is a need for an immunophenotype to easily identify and isolate the multipotent and highly efficient colony forming MSCs.

Bone marrow has been identified as a promising source of MSCs for regenerative medicine. They proliferate readily in culture, differentiate into various cell lineages, regulate the immune response, and promote the growth of host cells. The trilineage potential to exhibit adipo-, chondro-, and osteogenesis is a basic criterion for defining the multipotent MSCs desirable for therapeutic use. Thus, MSC therapies are under development to treat a broad range of diseases including myocardial infarction, renal failure, and osteoarthritis. The efficacy of these therapeutic applications is highly dependent on the intrinsic heterogeneity of MSC preparations. Single-cell analysis has revealed that MSCs are a heterogeneous mixture of cells that differ in their stage of lineage commitment and extent of differentiation. Despite its importance in defining potency, there have been only limited investigations of the heterogeneity in trilineage potential of MSCs and underlying hierarchical relationships. The hierarchy of MSC lineage commitment has been variously described as a sequential loss of adipogenic and then chondrogenic potential to yield osteogenic progenitors or MSCs that retain adipogenesis but not chondrogenesis. The ambiguity in this hierarchy is due, in part, to current difficulties in isolating multipotent MSCs from heterogeneous cultures.

There are no standardized procedures to isolate MSCs with a specific immunophenotype that is indicative of potency. The transcriptome and proteome expression profiles of MSCs are highly dependent on their culture conditions, and sorting MSCs according to light-scattering properties during flow cytometry provides only a partial identification of multipotent cells. Individual MSC cells have been isolated and their potency evaluated; however, a high-capacity format is required to obtain statistically significant results to identify the multipotent MSCs. Also, high-capacity assays have been developed to assess proliferation and differentiation to a specific lineage, such as chondrocytes, but they do not evaluate multipotency nor provide a method to retain large numbers of single-cell derived cultures for additional analysis once function has been determined. These limitations represent serious impediments to the therapeutic use of MSCs.

For autologous MSC therapies, the donor MSC preparation will be different for each patient. A barrier to realizing the therapeutic potential of MSCs is the variability in the regenerative capacity of MSCs from different donors. Donor variation in MSC preparations impedes the production of autologous MSC therapies with consistent efficacies among different patients. Also, allogenic MSC selection is hampered by the lack of a screening process for the multipotent cells capable of high proliferation. Currently, MSCs are identified and immunophenotyped by the expression of stromal antigens and absence of hematopoietic antigens. But these markers do not correlate to multipotency or highly efficient colony formation desirable for an MSC with therapeutic potential. Therefore, a method to screen and isolate MSCs from any source of mammalian stem cells with multipotency and high proliferation capability is desirable for therapeutic and research use.

SUMMARY OF THE INVENTION

The present invention provides a method of identifying multipotent MSCs capable of high proliferation. The multipotent cells can differentiate into osteogenic, adipogenic or chondrogenic cells. The MSCs can be harvested from either a donor or the patient for therapeutic use or other donors for investigative use, and this invention has both autologous and allogenic applications. MSCs from cell banks can also be used. Antibodies targeting CD146 and NG2 antigens conjugated with indicators are exposed to collection of heterogeneous stem cells. The attachment of these antibodies on the surface of stem cells indicates the presence of CD146 and/or NG2 antigens. The MSCs with the high expression of CD146, NG2 or a combination of both can be selected using flow cytometry or other selection techniques. The identification of the cells using the method of this invention poses minimal damage to the cells.

For patients with immediate need of multipotent MSCs with a high proliferation potential, the selected cells can be used immediately. The MSC selection by immunophenotyping of this invention also minimizes senescent cells and is selective for cells that are multipotent rather than committed to single or bi-tissue lineage. The cells with high expression of CD146 and/or NG2, also can have colony forming efficiency of greater than 40%, enhancing their potential for therapeutic use.

For patients or other use that does not require more immediate selection and isolation of multipotent MSCs capable of high proliferation, cells having the high expression of CD146 and/or NG2 can be selected and cultured. The cultured cells can be monitored, and a further selection of cells with the desired high expression of CD146 and/or NG2 can be isolated. Cells with high expression of CD146 and/or NG2 can be identified, isolated and further cultured to produce an enriched population of cells. This process can be repeated as desired. At any time during the culturing process, cells can be cryopreserved for future use. The invention can be used for all mammals including veterinary therapy and investigation and autologous and allogenic therapies.

BRIEF DESCRIPTION OF THE DRAWINGS

Nomenclature of Figures: CCMA refers to cell culture medium with antibiotics; GAG refers to glycosaminoglycans; OAC refers to tripotent cells; OA refers to osteoadipogenic cells; OC refers to osteo-chondrogenic cells; O refers to osteogenic.

DETAILED DESCRIPTION OF THE INVENTION

Figure 1:
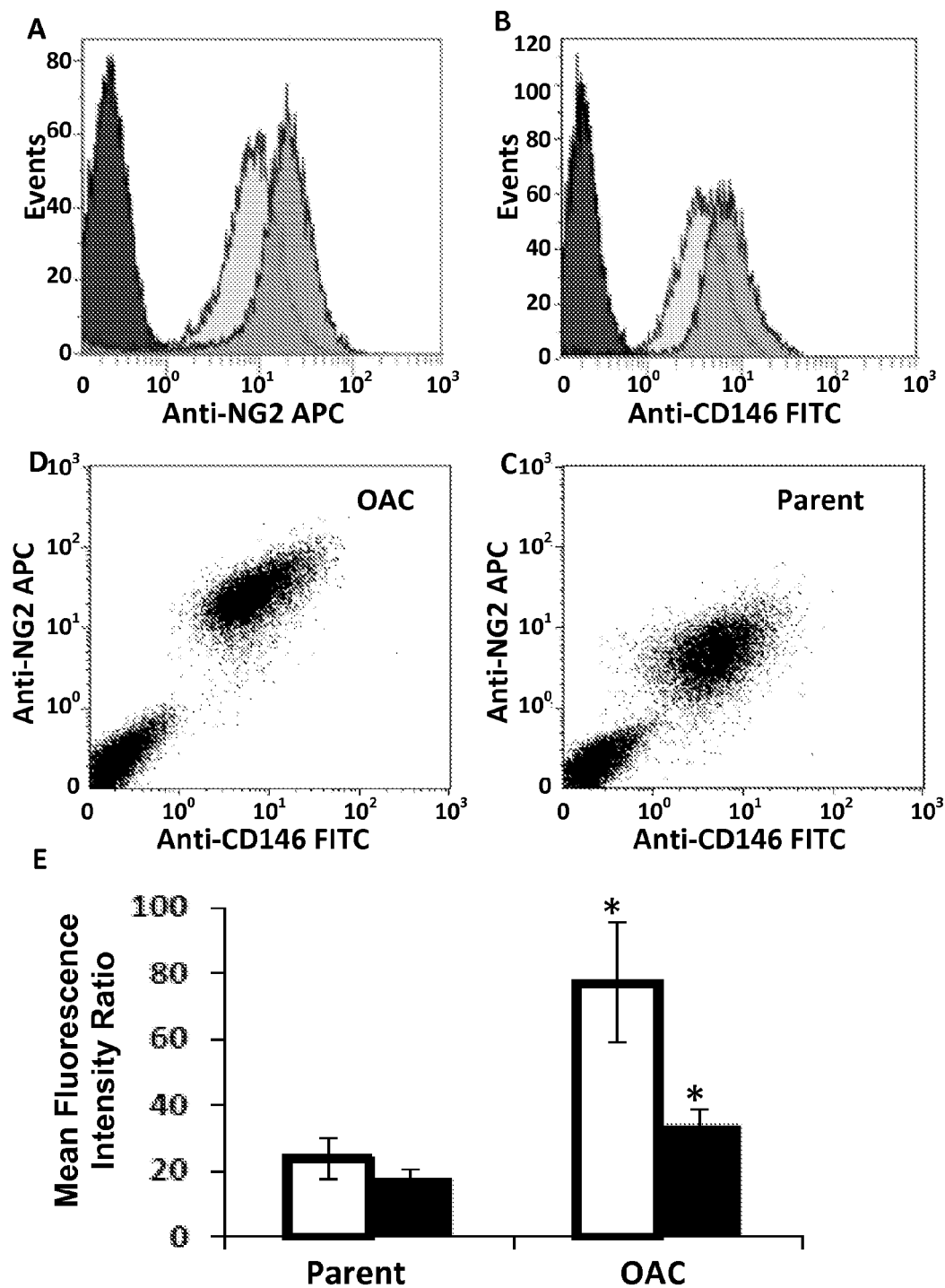
FIG. 1 Representative histograms for NG2 (A) and CD146 (B) expression in pooled multipotent MSC cells (dark grey) relative to parent population (light grey) and isotype control (black). Representative bivariate histograms representing NG2 expression vs. CD146 expression for multipotent (C) and parent (D) populations. Mean fluorescent intensity ratios (E) of NG2 (white) and CD146 (black) expression reported as mean±standard error of the mean (n=4 samples). *, $P<0.05$ vs. parent.

Detailed descriptions of one or more preferred embodiments or methods are provided herein. It is to be understood, however, that the present invention may be in various methods or forms. Therefore, specific details disclosed herein are not to be interpreted as limiting, but rather as a basis for the claims and as a representative basis for teaching one skilled in the art to employ the present invention in any appropriate manner.

The term stem cell or MSC refers to a cell that has the capacity for prolonged self-renewal, and can produce at least one type of differentiated descendent cell. Differentiation potential, used herein, refers to the ability of a stem cell to differentiate into descendent cells with various phenotypes. Stem cell and MSC may be used interchangeably according to context. Multi-potency refers to the ability of a cell to differentiate into multiple types of descendent cells specifically osteogenesis, adipogenesis and chondrogenesis. A uni-potent stem cell refers to stem cell that is only capable of differentiating into one type of descendent cell and bi-potent stem cell refers to a stem cell that is only capable of differentiation into two types of descendent cells. Senescent cells refer to cells that can no longer undergo mitotic division. CD146 refers to a cell adhesion molecule expressed on the surface of some stem cells. CD146 antibody refers to any antibody that binds to the CD146 antigen. This invention discloses the association of CD146 and/or CD146 expression and stem cell differentiation potential and colony-forming efficiency. NG2 refers to nerve/glial antigen 2, and is an antigen expressed on the surface of some stem cells. NG2 antibody refers to any antibody that binds to the NG2 antigen. This invention discloses the association between NG2 expression and stem cell differentiation potential. Immunophenotyping refers to the process of determining antigens or markers on a cell by monitoring antibody binding on cells. This process may be used to analyze the constituents and characteristics of a heterogeneous or any other type of cell culture. The term indicator, or indicator compound, may refer to any compound that is used for the purpose of identifying or marking the presence of antibodies, and the cells that are bound to the antibodies. Examples of indicators include dyes, fluorescent agents, or other compounds that can be detected and/or quantified.

MSCs that are tripotent express higher levels of CD146 and NG2 than the heterogeneous cell population from which the isolated cells were derived. CD146 (also known as MCAM, Mel-CAM, S-Endo-1, A32 antigen, and MUC18) is expressed on several cell types (e.g., MSCs, endothelial cells, and melanoma cells) and participates in heterotypic intercellular adhesion. NG2 is a chondroitin sulfate proteoglycan that spans the outer cell membrane. The higher expression of CD146 and/or NG2 in tripotent MSCs is in contrast to the expression of other cell surface proteins, such as CD44 and CD73, that is independent of differentiation potential of MSCs. The differential expression of CD146 and/or NG2 can be utilized to specifically amplify and/or enrich stem cells with desired differentiation potential, monitor the differentiation potential of a heterogeneous stem cell population, quantify the heterogeneity in differentiation potential of a stem cell culture, and remove stem cells with specific differentiation potentials from a heterogeneous cell culture.

The invention described addresses a basic deficiency in stem cell technology by developing a quantitative and high-capacity assay to determine the differentiation potential of a heterogeneous stem cell population. This technology has numerous applications given the importance of heterogeneity to the therapeutic and research potential of MSCs. The insight into MSC populations that can be attained with this technology will ultimately enable control over the composition and, thus, the efficacy of MSC therapies.

Stem cells used in this method are extracted from a donor or a patient. Alternatively, the stem cells may be obtained from a cultured cell colony or a heterogeneous culture. Non-specific antigens on the stem cells are blocked with albumin. The cells are subsequently incubated with CD146 antibodies, NG2 antibodies or both. The CD146 and/or NG2 antibodies are conjugated with an indicator compound. After sufficient time has passed to allow binding of CD146 and NG2 antibodies to any CD146 or NG2 antigens present, unbound antibodies are removed. The presence of either the CD146, CD146 conjugated indicator compounds and/or NG2, NG2 conjugated indicator compounds and after unbound antibodies are removed will indicate the differentiation potential for multipotent MSCs with high proliferation potential. High expression of CD146 and NG2 alone and in combination is used for selection of MSCs with high proliferation and multipotency.

The multipotency potential of MSCs is monitored by observation of CD146 and NG2 antigen expression. CD146 and NG2 antibodies conjugated with an indicator compound are incubated with the stem cells. CD146 and NG2 antibodies will selectively bind to stem cells that express CD146 and NG2 antigens. The loss of multi-lineage potential in MSCs is further associated with a change in CD146 and NG2 expression, and a corresponding change in CD146 and NG2 antibody binding. The unbound antibodies can be removed continuously, or at discrete time intervals. The binding of CD146 and/or NG2 antibodies, which may be indicated by the conjugated indicator compounds, can be used to monitor the differentiation potential of the MSCs continuously or at discrete times during the culturing of MSCs.

Intercellular communication may be controlled by selectively removing stem cells that promote undesirable changes to a cell culture. Uni-potent cells and senescent cells, in particular, are associated with promoting cell culture changes via intercellular communication, and their presence may adversely affect the culture for multipotent cells. These stem cells may be identified by their lack of CD146 and/or NG2 antibody binding characteristics, and removed from a stem cell culture.

An alternate method to enrich multipotent MSCs from heterogeneous MSC cultures can utilize cell migration through a porous membrane. The membrane may be coated with substrates for CD146, NG2 or a combination of the two markers. An example of a substrate is collagen VI for NG2 but any substrate known in the art may be used. The heterogeneous MSC culture is placed on one side of the membrane, and a chemotactic agent that promotes cell migration is placed on the other side of the membrane. An example of a chemotactic agent is serum, when used in combination with a serum-free MSC culture. Multipotent MSCs with high expression of the antigen (i.e., CD146, NG2 or their combination) that binds to the substrate migrate more quickly through the porous membrane than lineage-committed MSCs with low expression of the antigen. The migrated cells are an enriched culture of multipotent MSCs. The MSCs that migrate more quickly can be collected and used as desired for therapy or research.

The cells selected with high expression of CD146 and/or NG2 may be cryopreserved for future use. In one embodiment, stem cell colonies are added to a microplate containing a freezing media. One example of a freezing media included 65% CCMA, 27% FBS, and 8% DMSO. Paraffin oil may be added to the top of each well to prevent $CO_2$ degassing and medium evaporation. The microplate containing stem cell colonies is frozen. In one embodiment, the temperature of the microplate is maintained at −80° C. To recover the stem cells for use, the plates are thawed and allowed to recover for 3 days. The recovered stem cells may be seeded into micro-plates and amplified.

The invention can be used in combination with any other indicator to detect lineage-committed (non-multi-potent) and/or senescent MSCs. The indicator would be strong for lineage-committed MSCs and weak for multipotent MSCs. Examples of indicators include fluorescent proliferation dyes and cell-surface antigens that are upregulated on lineage-committed and/or senescent MSCs. Proliferation dyes are characterized by long-term retention in cells. During each cell division, the amount of dye is divided between the two daughter cells. Each subsequent generation receives half the fluorescence of the parent cells. Slow-growing lineage-committed and senescent MSCs will stain strongly for these proliferation dyes; whereas, rapidly dividing multipotent MSCs would be weakly stained. These indicators can be used in combination with the markers of this invention. The multipotent MSCs will have high expression of CD146 and/or NG2 and be weak for an indicator of lineage-committed and/or senescent MSCs. This combination can be useful in removal of lineage-committed and/or senescent MSCs from heterogeneous MSC cultures and in further enriching multipotent MSCs from heterogeneous MSC cultures.

The following is the immunophenotyping process used, but the process can be accomplished by any method available to those skilled in the art. Trypsinized MSCs were washed by centrifugation in PBS. Nonspecific antigens were blocked by incubating the cells at $10^6$ cells/ml in PBS containing 1% bovine serum albumin for 20 minutes at 37° C. Aliquots of 100 µl cell suspension were incubated at 4° C. for 20 minutes with fluorochrome-conjugated, anti-human monoclonal antibodies. Labeled samples were washed by centrifugation in three volumes of phosphate-buffered saline (PBS). Isotype controls were run in parallel at the same concentration used for each antibody. The immunophenotype of MSCs was evaluated with a FC500 flow cytometer (Beckman Coulter, Fullerton, Calif. (http://www.beckmancoulter.com). The cells for this method conform to the criteria for MSCs specified by the International Society of Cellular Therapy. Specifically, the cells were attachment-dependent, exhibited trilineage potential, expressed an immunophonotype that is characteristic of MSCs (e.g., CD73+, CD90+, and CD105+), and were negative for cell-surface epitopes indicative of hematopoietic cells (e.g., CD19−, CD34−, and CD45−).

The MSCs used for screening for high expression of CD146 and NG2 can be from a donor, cell colony or heterologous source. The MSCs to be screened for CD146 and NG2 are incubated as described above with NG2: Anti-NG2-allophycocyanin from R&D Systems, catalog #FAB2585A, clone #LHM-2 and CD146: Anti-CD146-FITC from eBioscience, catalog #11-1469, clone #P1H12. The antibody binding capacity (ABC) of these antibodies correlates to colony-forming efficiency as well as multipotency for MSCs. ABC values are measure of the molecules of antigen on the cell surface, in this invention CD146 and/or NG2, and are specific to the antibody used.

The desired colony forming efficiency is greater than 40% to provide stem cells that will multiple efficiently and provide the best outcome for patients in need of stem cell therapy or provide a population for research. Also, the stem cells with high expression of CD146 and/or NG2 are capable of the desired differentiation into other cell types as previously described. ABC can be used to screen for multipotent MSCs with high colony forming efficiency from donors, the patient or cell banks. For a colony-forming efficiency greater than 40%, ABC values can be at least about 100,000 molecules of antibody per cell for NG2. For CD146, this value can be at least about 200,000 molecules of antibody per cell. Another measure used for screening for the desired MSCs is the molecules of equivalent soluble fluorochrome (MESF) value. For multipotent MSCs the MESF value is at least about 100,000 molecules of fluorochrome per cell for CD146 and at least about 200,000 molecules of fluorochrome per cell for NG2.

FIG. 1 is representative histograms for NG2 (FIG. 1A) and CD146 (FIG. 1B) expression in pooled multipotent cells (dark grey) relative to parent MSC population (light grey) and isotype control (black). The representative bivariate histograms depict NG2 expression vs. CD146 expression for multipotent (FIG. 1C) and parent (FIG. 1D) populations. Mean fluorescent intensity ratios (FIG. 1E) of NG2 (white) and CD146 (black) expression in the multipotent cells (OAC) are shown as compared to the mean±standard error of the mean for the heterogeneous parent culture from which the multipotent cells were derived (n=4 samples). *, P<0.05 vs. parent. The high expression of CD146 and NG2 in the multipotent MSCs is illustrated in FIG. 1.

Figure 2:
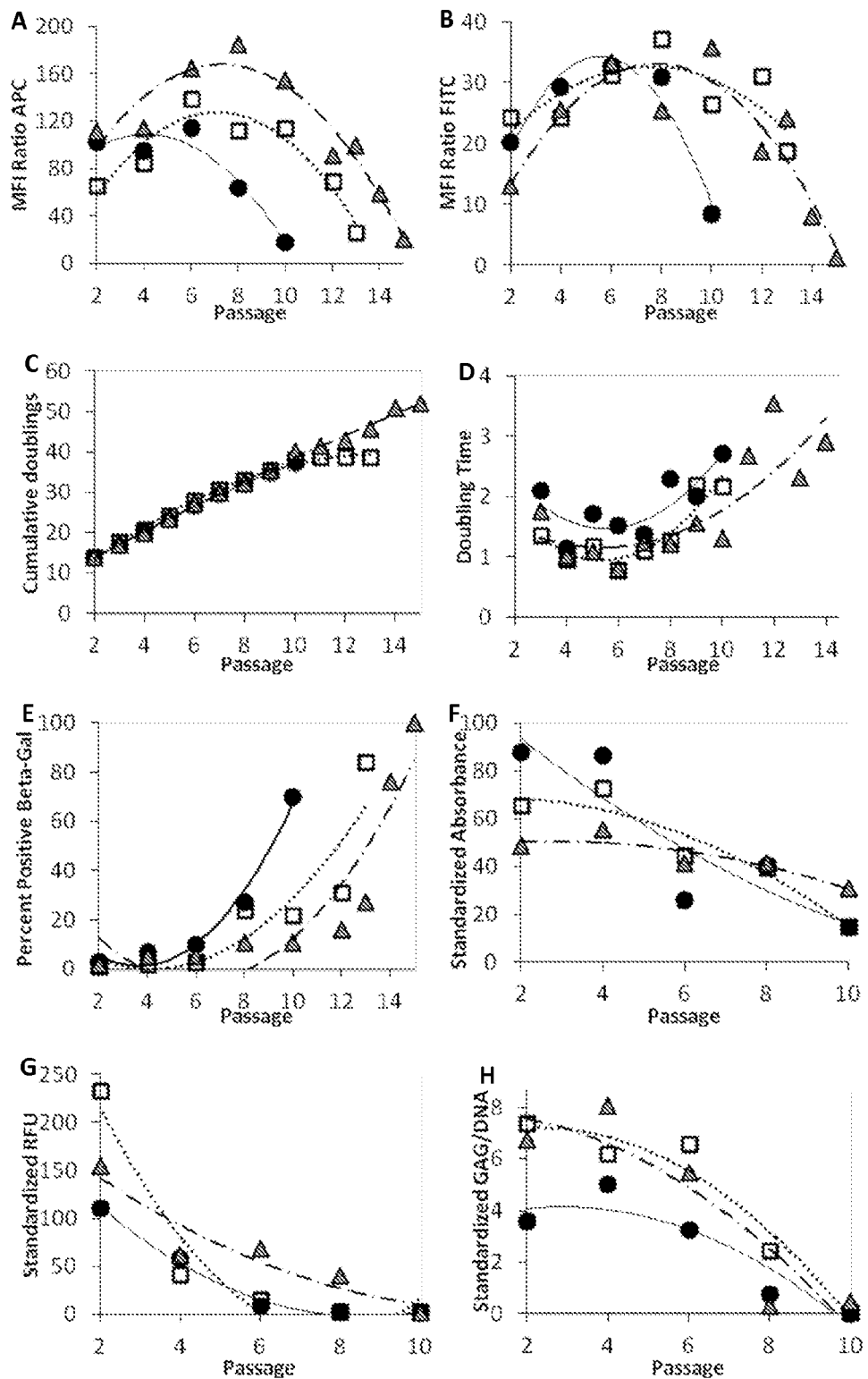
FIG. 2 Passaging effects on multipotent MSCs. NG2 (A) and CD146 (B) expression was determined with respect to passage number for pooled multipotent MSCs. In addition, growth properties were evaluated by monitoring cumulative doublings (C), doubling times (D) and beta-galactosidase expression (E) at each passage. Osteogenesis (F), adipogenesis (G) and chondrogenesis (H) was observed to verify loss in trilineage potential during passaging.

FIG. 2 is a study on the passaging effects while culturing multipotent MSCs. NG2 (FIG. 2A) and CD146 (FIG. 2B) expression was determined with respect to passage number for multipotent MSCs. Each line of geometric figures represents pools (n=5) of single-cell derived cultures of MSCs prepared as described below. In addition, growth properties were evaluated by monitoring cumulative doublings (FIG. 2C), doubling times (FIG. 2D) and beta-galactosidase expression to determine cell senescence (FIG. 2E) at each passage. Osteogenesis (FIG. 2F), adipogenesis (FIG. 2G) and chondrogenesis (FIG. 2H) was observed. The decrease in CD146 and NG2 expression correlates to the loss in trilineage potential during passaging of MSCs in culture.

MSCs with high expression of CD146 and/or NG2 can be isolated for immediate use. In the alternative, the cells with high expression can be cultured as described below and monitored for expression of CD146 and/or NG2. The isolated and cultured MSCs with the desired level of CD146 and/or NG2 can be isolated and further cultured to produce enriched MSCs with the desired characteristics of multipotency and high colony-forming efficiency. The selection criteria, culturing and preservation are described herein. FIG. 2 illustrates the presence of CD146 and NG2 during culture in order to provide the best multi-potency potential. The MSCs with high levels of expression can be further selected for use and/or continued culture for an enriched MSC population. Also, the enriched MSCs can be either cryopreserved at the time of isolation or cultured and cryopreserved for future use.

An alternative method of this invention use to confirm the potency and colony formation of cells with the markers for CD146 and NG2 utilizes individual cells that can be isolated from a donor, cell colony or heterogeneous culture. The following articles are incorporated by reference in their entirety: In Vitro High-Capacity Assay to Quantify the Clonal Heterogeneity in Trilineage Potential of Mesenchymal Stem Cells Reveals a Complex Hierarchy of Lineage Commitment, Russell et al., 28 *Stem Cells* 788-798 (2010); Clonal Analysis of the Proliferation Potential of Human Bone Marrow Mesenchymal Stem Cells as a Function of Potency, Russell et al., 108 *Biotechnology and Bioengineering* 2716-2726 (2011).

This method can be used to isolate single cells for culturing. If small number of MSCs are desirable for use or study, this alternative method can be used. Since the source of the multipotent MSCs are a single cell that will be passaged from about 2 to 15 times (10-50 doublings), the number cells available for use are fewer than the method described above. This method can also be used to identify other markers that may indicate multipotent cells with high proliferation potential in addition to CD146 and NG2. The MSCs were sterilely labeled in situ for 10 minutes with 5 µM CellTracker Green, 5-chloromethylfluorescein diacetate ($\lambda ex/\lambda em$=492/517 nm), in serum-free CCMA pre-warmed to 37° C., according to Invitrogen's instructions. After trypsinization, MSC single cells were generated by limiting dilution into a 96-well microplate containing 50 µl/well of fresh CCMA and 75 µl/well of CCMA conditioned by MSCs for 48 hours and sterile-filtered (0.2 µm pore size) to remove any suspended cells. Each well was examined with a fluorescent Olympus IX50 microscope (Olympus America, Center Valley, Pa., http://www.olympusamerica.com) to determine the plating efficiency as the percentage of wells inoculated with a single cell. Fifty microliters of fresh CCMA was added to each well 3 days after inoculation and 50 µl of medium was replaced with fresh CCMA after an additional 3 days. On day 7 of cultivation, colony-forming efficiency was calculated as the percentage of MSC colonies originating from a single cell, divided by the fraction of viable cells in the inoculum. Colonies derived from single cells containing at least 300 cells/well were subcultured at a 1:4 ratio to evaluate trilineage multi-potency potential.

The MSCs from single-cell derived colonies or other isolated MSCs from donors or cultures can be cryopreserved by adding 50 µl of the trypsinized cell suspension to a fresh 96-well microplate containing 50 µl/well of 2× freezing media (65% CCMA, 27% FBS, and 8% dimethyl sulfoxide (DMSO). To inhibit degassing of $CO_2$ and medium evaporation, 100 µl of filter-sterilized light paraffin oil can be added to the top of each well, and the lid was secured with parafilm. The plate(s) can be transferred to a Styrofoam box, frozen at −80° C. for about 8 hours and then placed directly into a −80° C. freezer for long-term storage. As little as 75 cells/well have been frozen by this method. Plates can be defrosted in a 37° C. incubator, and thawed cell suspensions transferred to 24-well plates containing 1 ml of fresh CCMA/well. A day after inoculation, the medium was exchanged with fresh CCMA for routine cell amplification.

Frozen MSC cells cultured from a single cell were thawed and amplified for 3 days (~2×10$^3$ cells/single-cell colony), and their potency was verified. The efficiency of P3 amplified MSC cells to form colonies when inoculated at 100±10 cells in a 10-cm tissue-culture dish was evaluated using crystal violet staining to detect cell colonies. For growth kinetics, P3 MSC cells cultured from a single cell were inoculated at 100±10 cells/cm$^2$ in 24-well plates containing 0.5 ml CCMA/well, with complete medium exchange every other day. Cell concentration was measured by hemocytometer counting, and specific growth rate was evaluated as in Blanch and Clark, *Biochemical Engineering*, New York, Marcel Dekker, p. 702. (1997).

After subculturing, MSC single-cell derived colonies were expanded for 7 days in 96-well microplates containing 150 µl/well of CCMA until ~75% confluent. The assay quantifies the trilineage potential of MSC single cells to exhibit adipo-, chondro- and osteogenesis as a measure of potency. Osteogenesis was induced by cultivation in low-glucose Dulbecco's MEM supplemented with 10% FBS, 100 nM dexamethasone (Sigma-Aldrich, St. Louis, Mo.), 10 mM β-glycerophosphate (Sigma-Aldrich) and 50 µM L-ascorbic acid 2-phosphate (Sigma-Aldrich). After 21 days of differentiation, confluent monolayers were fixed in 4% paraformaldehyde for 20 min and stained with 1% Alizarin Red S (pH 4.2, Sigma-Aldrich) for 20 min to detect mineralized extracellular matrix. Stain was extracted with 100 µl/well of 10% cetylpyridinium chloride in 10 mM sodium phosphate buffer (pH 7.0) for 15 min, and the spectral absorbance was measured at 562 nm.

To induce adipogenesis, single-cell derived colonies were expanded as described above and cultivated for 21 days in CCMA supplemented with 0.5 µM dexamethasone, 0.5 mM isobutylmethylxanthine (Sigma-Aldrich) and 50 µM indomethacin (Sigma-Aldrich). Lipids were detected by adding 5 µl AdipoRed reagent (Lonza, Walkersville, Md.) to the cell monolayer in 200 µl PBS/well. Fluorescence was measured after 10 min with excitation of 485 nm and emission of 535 nm.

For chondrogenesis, single-cell derived colonies were amplified for nearly 2 weeks in 6-well plates containing 2 ml CCMA/well. Pellet cultures were formed by inoculating 2±0.2×10$^5$ cells/well in 96-well, V-bottom polypropylene microplates (Thermo Fisher Scientific, Waltham, Mass.) containing 200 µl/well CCMA. The next day, CCMA was replaced with differentiation medium consisting of high-glucose Dulbecco's MEM supplemented with 100 ng/ml bone morphogenetic protein-2 (R&D Systems, Minneapolis, Minn.), 10 ng/ml transforming growth factor-β3, 100 nM dexamethasone, 50 µg/ml L-ascorbic acid 2-phosphate, 100 µg/ml pyruvate (Sigma-Aldrich), 40 µg/ml1 proline (Sigma-Aldrich) and 10 µl/ml ITS+ (BD Biosciences, San Jose, Calif.). After 21 days of differentiation, the amount of sulfated glycosaminoglycans (GAGs) in digested cell pellets was quantified with 1,9-dimethylmethylene blue (Sigma-Aldrich), using chondroitin sulfate A for calibration. GAG content is reported on a per mass DNA basis by quantitation of DNA in digested pellet samples with Hoechst 33258 (Sigma-Aldrich), employing calf thymus DNA (Sigma-Aldrich) as the calibration standard.

Images of stained histological samples of differentiated MSCs to view the cell types were captured with an Optronics DEI-750 digital camera (Optronics, Goleta, Calif., http://www.optronics.com) mounted onto an Olympus IX50 microscope. Staining was evaluated in terms of the product of the percent stained area and its optical density. 4 Areas of positive staining and projected 2D areas of MSCs in culture were traced using a Graphire 4 CTE-640 tablet (Wacom Technology Corp., Vancouver, Wash., http://www.wacom.com) and analyzed with the Area, Percent Area and Optical Density options in the Count/Size and Draw tools of Image-Pro Plus software Version 6.1 (Media Cybernetics, Crofton, Md., http://www.mediacy.com). Optical density was calculated on a scale of 0 (white) to 2.5 (black) relative to the corresponding negative control using the Background Correction option. Imaging results are reported as a mean value from 20-50 randomly selected images on average per culture sample.

Figure 3:
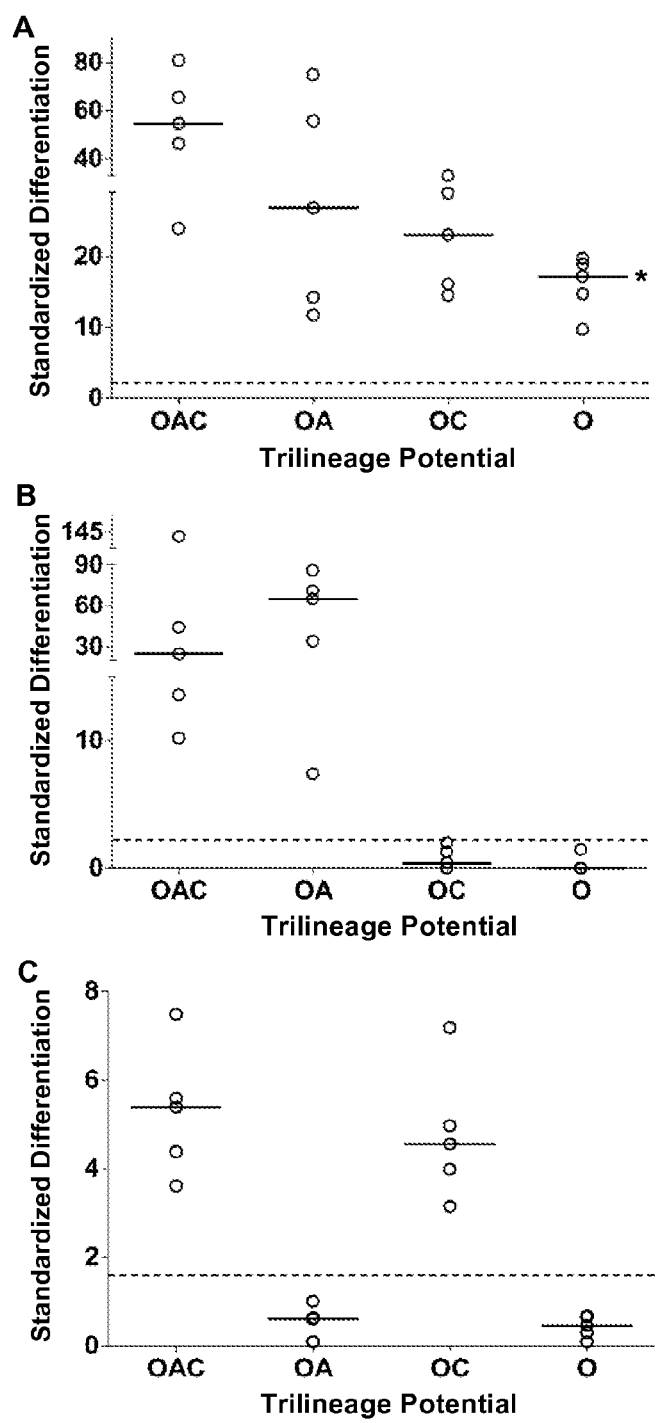
FIG. 3 Representative potency of amplified MSC single-cell derived cultures. Trilineage potential of MSCs was verified upon inoculating experimental cultures. Three matched cultures derived from a single cell were stained after 21 days in differentiation medium with Alizarin Red S to detect mineralization of extracellular matrix for osteogenesis (A); AdipoRed, lipids for adipogenesis (B); and 1,9-dimethylmethylene blue, sulfated GAGs for chondrogenesis (C). Negative control: MSCs in CCMA. Dimensionless differentiation scores were standardized relative to the mean±standard deviation for the negative controls of 0.19=0.04 absorbance units (A), 2200±400 relative fluorescence units (B), and 0.26±0.07 µg GAG/µg DNA (C). Threshold values for positive differentiation (dashed lines) correspond to the 95th percentile of the probability density for the negative controls. Median (-, n=5 MSCs). *$P<0.05$ vs. OAC MSCs.

FIG. 3 summarizes the multipotency of the cultured MSCs for osteogenesis (FIG. 3A) adipogenesis (FIG. 3B) and chondrogenesis (FIG. 3C) after 21 days of inducement in the differentiation media described above. Threshold values for positive differentiation (dashed lines) correspond to the 95th percentile of the probability density for the negative controls.

Figure 4:
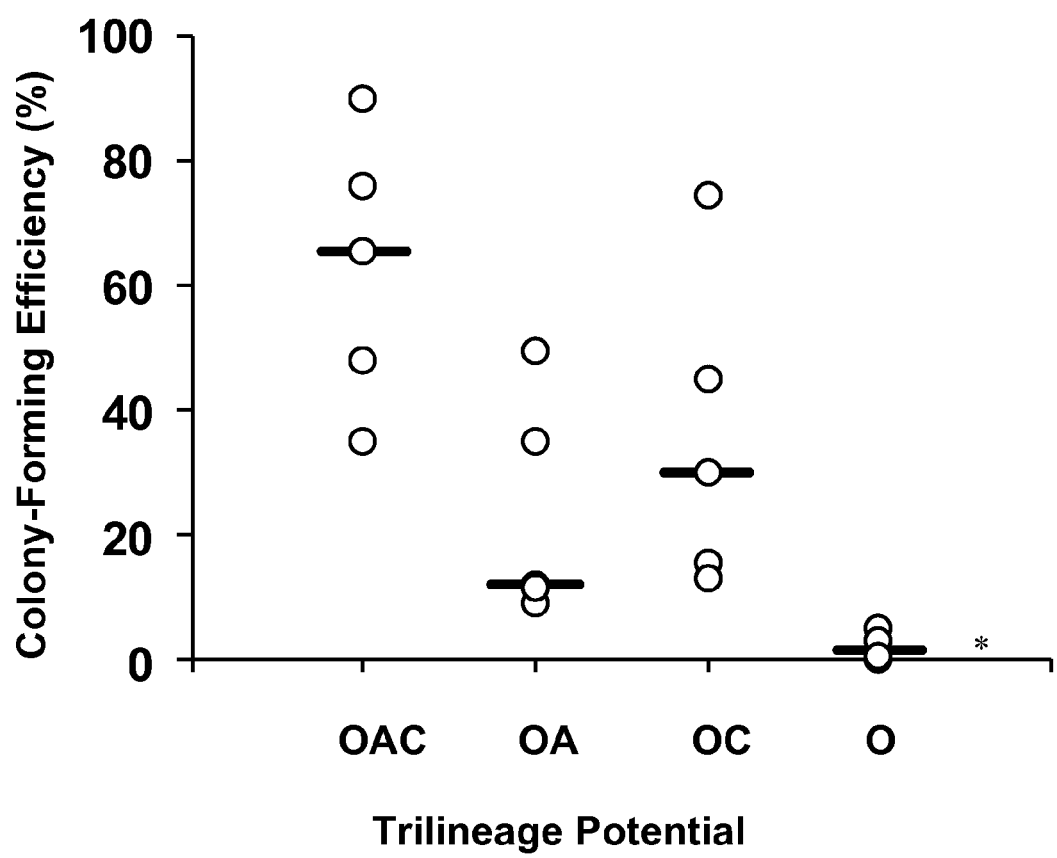
FIG. 4. Colony-forming efficiency of MSC cells as a function of trilineage potential. Cells were frozen in situ within 96-well microplates, thawed, and amplified to obtain ~2×10$^3$ cells (Passage 3). Potency of the expanded cells was confirmed. Colony-forming efficiency was calculated as the percentage of P3 MSC cells to form colonies when inoculated at 100±10 cells in a 10-cm culture dish containing CCMA. After 2 weeks of cultivation, colonies were detected by crystal violet staining Median (-, n=5 cells). *$P<0.01$ vs. OAC cells.

Colony-forming efficiency was evaluated by limiting dilution of fluorescently labeled MSCs which readily formed colonies under these conditions. The tracker dye CellTracker Green facilitated cell detection in wells on a 96-well microplate. The dye had negligible cytotoxicity: the viability of the inoculum was 90±4%. The cells with colony forming potential of greater than 40% can be identified. FIG. 4 shows the higher colony formation of the multipotent MSCs. As shown in FIG. 4 the desired colony-forming efficiency of 40% is often exceed by the multipotent MSCs.

To quantify DNA content of MSC cultures, 100 µl of papain-digested cell samples was mixed with 200 µl 0.1 M NaOH, incubated at room temperature for 30 minutes, and then neutralized by the addition of 200 µl 0.1 M HCl in 5 M NaCl, 100 mM sodium phosphate. In a 96-well microplate, 100 µl of the sample was added to 100 µl of 0.7 µg/ml Hoechst 33258 (Sigma-Aldrich) in 10 mM Tris buffer containing 200 mM NaCl and 1 mM EDTA (pH 7.4). Fluorescence was measured with excitation of 340 nm and emission of 465 nm. A standard curve was prepared with calf thymus DNA (Sigma-Aldrich).

The trilineage potential of single-cell derived cultures of MSCs was evaluated using the differentiation conditions specified above. Single-cell colonies were subcultured at a 1:4 ratio into replicate microplates: three plates were employed to evaluate trilineage potential; the fourth was frozen to preserve a template of MSCs cells for future use. MSC cells were designated as positive for differentiation if their standardized measurement exceeded the 95th percentile of the estimated probability density for the negative controls. The values were 1.9±0.2, 2.1±0.1, and 1.6±0.3 standard deviations for osteo-, adipo-, and chondrogenesis, respectively.

Growth kinetics of MSCs cells during ex vivo expansion on tissue-culture plastic is presented in FIGS. 5A, 5B, 5C and 5D. An inoculation density of 100 cells/cm$^2$ was selected. There were no significant differences among the four potency groups in the fraction of MSCs that survived in culture 24 h after inoculation and in the duration of the lag phase, with median values of 60% and 1 day (n=20), respectively, for all four groups (FIGS. 5A, 5B, 5C and 5D). After 10 days of expansion, cultures inoculated with tripotent MSCs expanded 200-fold (n=5) to 2–10×10$^4$ cells/cm$^2$ (FIG. 5A) and were 85% to 100% confluent (FIG. 5E). Lineage commitment limited ex vivo expansion of cultured MSCs. When inoculated with O cells, cultures accumulated <10$^3$ cells/cm$^2$ (FIG. 5A) and were ≤15% confluent (FIG. 5E) over the same period (P<0.001). Trends in specific growth rates as a function of MSC potency (FIG. 5F) are similar to those for colony-forming efficiency (FIG. 4). Of the four potency groups, tripotent inocula of OAC cells exhibited the highest proliferation potential with a median specific growth rate of 0.85 day$^{-1}$ (n=5), equivalent to a 20 h doubling time (FIG. 5F). The median specific growth rate was 5-fold less for cultures inoculated with O cells (P<0.01). Bipotent inocula exhibited an intermediate proliferation potential between these two extremes, with comparable median specific growth rates for OA and OC MSCs (0.50-0.60 day$^{-1}$).

Figure 5:
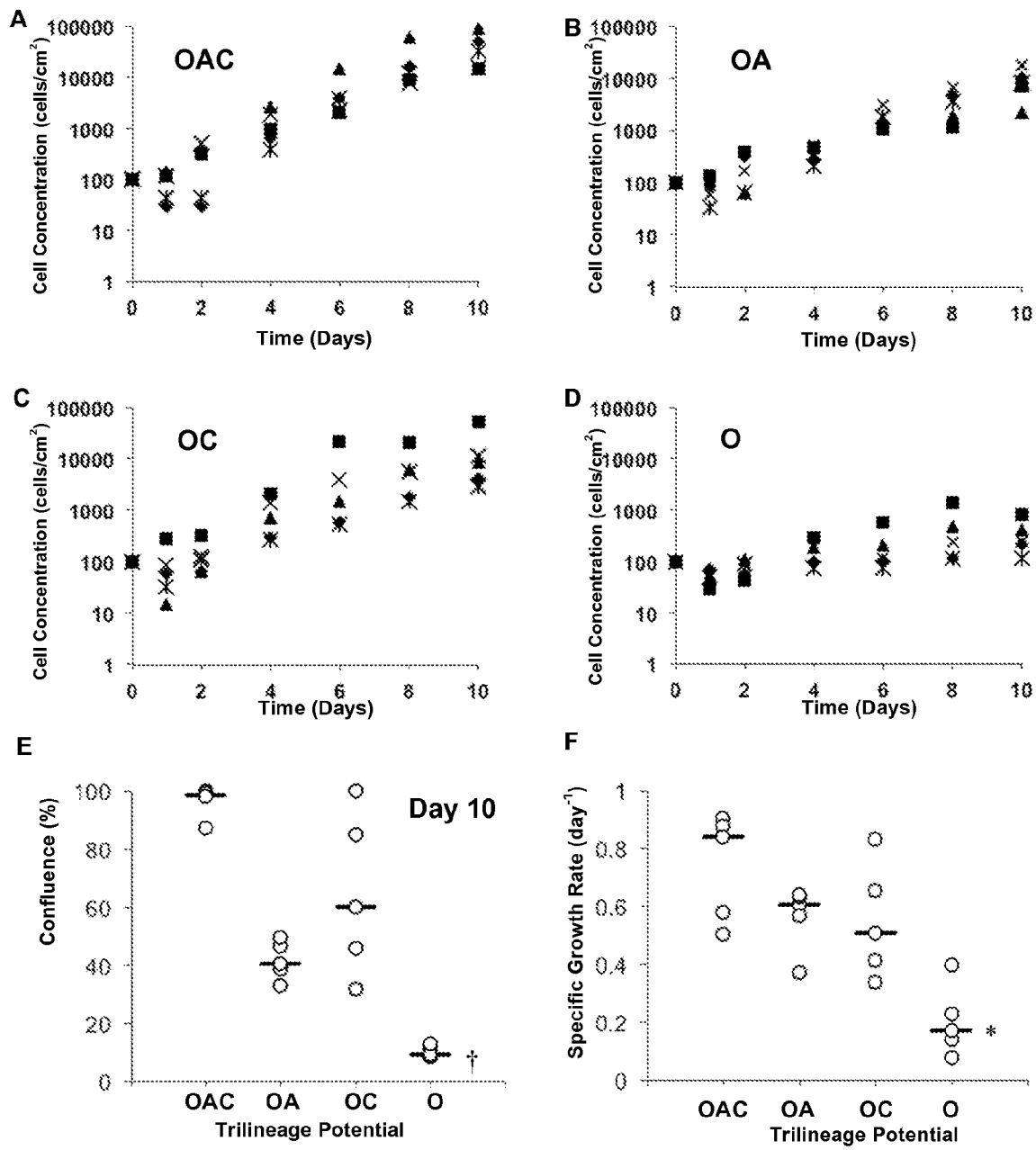
FIG. 5. Ex vivo expansion of MSC cells. P3 MSC cells were inoculated at 100±10 cells/cm$^2$ into 24-well plates and cultivated in CCMA for 10 days. Growth profiles of individual MSC cultures inoculated with OAC (A), OA (B), OC (C), and O (D) cells (n=5 cells). Percent confluence (E) on day 10 as determined by image analysis of culture surface (n=30 images/culture). Specific growth rates (F) corresponding to growth profiles in A–D. Median (-, n=5 cells). *$P<0.01$ and † $P<0.001$ vs. OAC cells.
Figure 6:
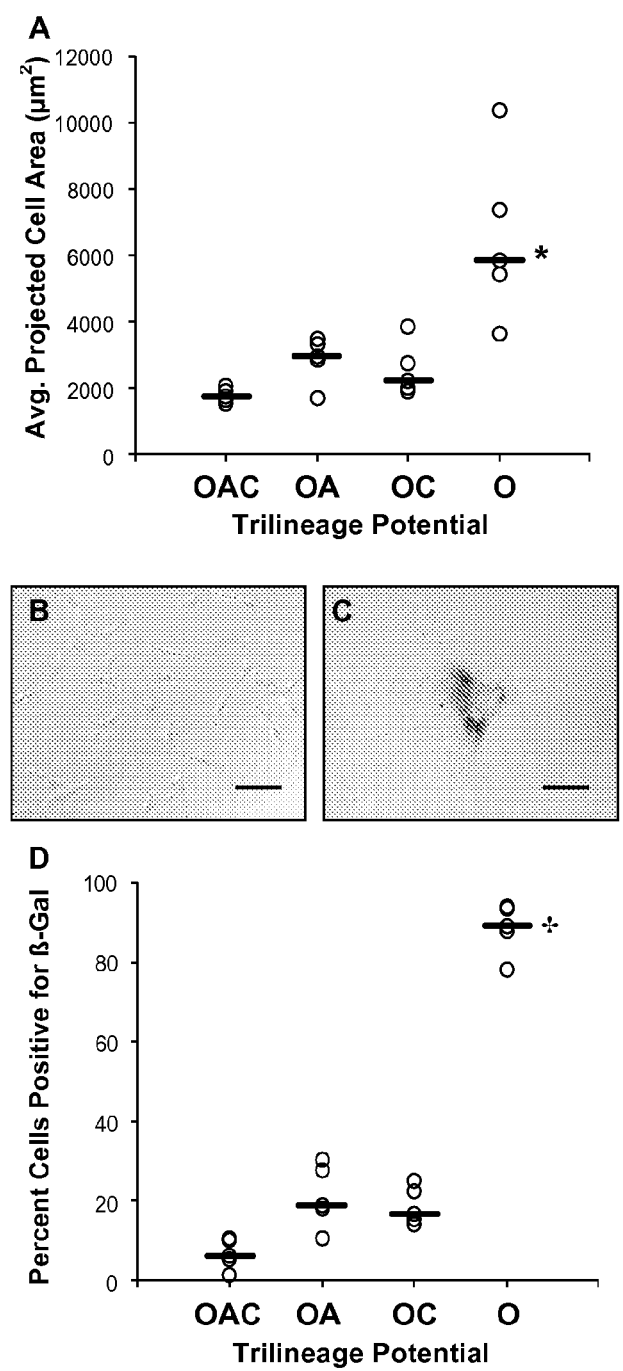
FIG. 6. Phenotyping cellular senescence in MSC cells as a function of trilineage potential. Senescence of MSC cultures depicted in FIG. 5 was evaluated on day 4 of cultivation when cells were subconfluent. Cell size (A) was assessed with image analysis as the average projected 2D area of MSCs on the culture surface (n=30 images/culture). Representative phase-contrast images displaying cell size and staining of senescence-associated β-galactosidase (β-Gal) activity at pH 6.0 in MSC cultures inoculated with OAC (B) and O cells (C). Percentage of β-Gal-positive MSCs (D) as determined by image analysis. Median (-, n=5 cells). *$P<0.01$ and †$P<0.001$ vs. OAC cells. Scale bars: 100 µm.

O cells expressed a phenotype indication of cellular senescence. Cell size was estimated by image analysis of the projected area of MSCs on a subconfluent culture surface (n=30 images/culture). MSC cultures inoculated with O MSCs contained cells with an average projected area of >3.6×10$^3$ μm$^2$/cell (n=5 cultures) on day 4 (FIG. 6A), equivalent to a cell radius of >34 μm (FIG. 6C). More than 75% of these lineage-committed MSCs stained positive for senescence-associated β-galactosidase activity at pH 6.0 (FIG. 6D). Positive β-galactosidase staining in subconfluent MSCs suggests irreversible growth arrest from senescence rather than a reversible, quiescent state in confluent cells. Tripotent inocula produced cultures with a healthy morphology (FIGS. 6A and 6B) and negligible β-galactosidase staining (FIG. 6D); whereas, bipotent inocula exhibited an intermediate phenotype of senescence (FIGS. 6A and 6D), consistent with the pattern observed for proliferation potential (FIGS. 4 and 5F).

The multipotent cells with high expression of CD146 and NG2 also indicate a lack of cell senescence-associated β-galactosidase activity (FIG. 6D). The feature is an additional aspect of the invention. The cells were tested at pH 6.0 was detected histochemically in subconfluent cultures for growth kinetics, 4 days after inoculation, with the Senescence β-galactosidase Staining kit (Cell Signaling Technology, Danvers, Mass.).

Figure 7:
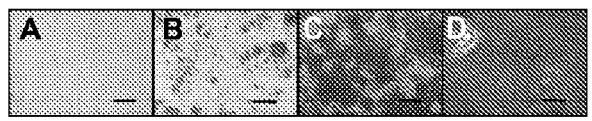
FIG. 7. Correlations between histological staining of mesenchymal stem cells (MSCs) and standardized measurements of osteo-(A-E), adipo-(F-J), and chondrogenesis (K-O). Representative histological samples stained with Alizarin Red (A-D), AdipoRed (F-I), and Alcian Blue (K-N): negative control (A, F, K); osteogenic MSC cells with average standardized absorbance of 4.3 (B), 30 (C), and 44 (D); adipogenic cells with average standardized fluorescence of 73 (G), 190 (H), and 510 (I); and chondrogenic cells with average standardized µg GAG/µg DNA of 4.4 (L), 10 (M), and 37 (N). Scale bars: 100 µm. Correlation graphs: cells are designated positive (▲) or negative (○) for differentiation based on a 95% confidence level with standardized scores of 1.9±0.2 for osteogenesis (E), 2.1±0.1 for adipogenesis (J), and 1.6±0.3 for chondrogenesis (O). Inserted graphs are plotted on an expanded scale. Negative control: MSCs in complete culture medium.
Figure 7:
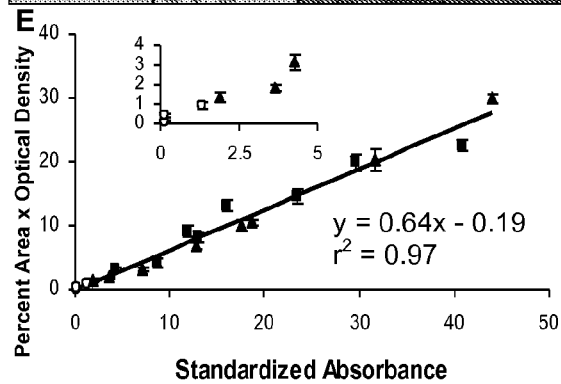
Figure 7:
Figure 7:
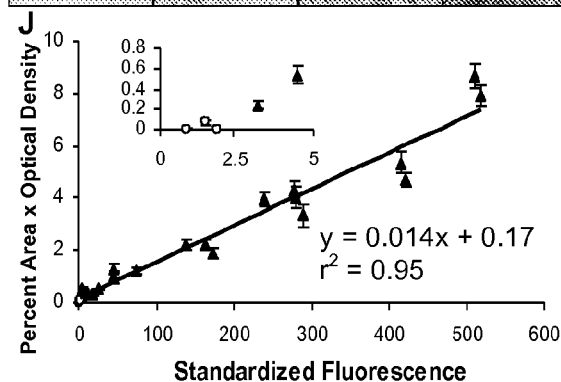
Figure 7:
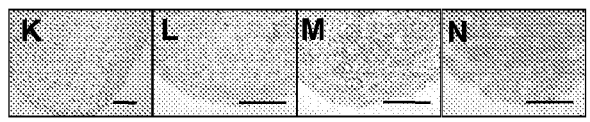
Figure 7:
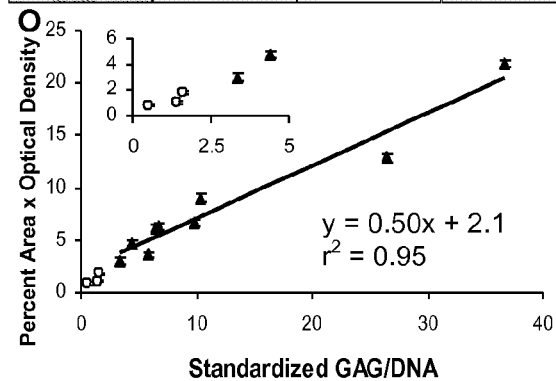

Correlations were established to relate standardized differentiation measurements to histological staining of differentiated MSCs (FIG. 7). The histological samples were monolayers for osteo- and adipogenesis (FIGS. 7A-E and 7F-J) and sectioned pellets for chondrogenesis (FIG. 7K-O). Staining was evaluated in terms of the product of the percent stained area and its optical density. This area-times-intensity score was ≤30 for osteogenesis (FIG. 7A-E), ≤10 for adipogenesis (FIG. 7F-J), and ≤25 for chondrogenesis (FIG. 7K-O). The higher percentages for osteo- and chondrogenesis may be due to staining extracellular versus intracellular markers and/or a greater degree of differentiation. Linear regression models were sufficient to fit the data in all cases. From these equations, the 95th percentile threshold for positive differentiation corresponds to an area-times-intensity score of 1.0±0.1, above which single-cell derived cultures were designated as positive for osteogenesis. The cutoff values for adipo- and chondrogenesis were equivalent to scores of 0.20±0.01 and 2.9±0.2, respectively. In all three cases, the threshold area-times-intensity scores were at least 8-fold less than the maximum values observed for positive cells. The single-cell cultures positive for multipotency have high expression of both CD146 and NG2 as described herein.

To overcome current limitations in multipotent MSC identification, the new efficient high-capacity assay has been developed for use with any sample of heterogeneous MSCs. The method can be used to screen MSCs simply using the markers for CD146 and NG2. The ability of the assay to isolate cells of known potency and quantify MSC heterogeneity will improve the efficacy of MSC therapies.

Flow cytometry confirms the higher expression of the cell surface antigen NG2 in multipotent vs. parent MSCs, with ~3-fold difference in mean fluorescent intensity (p<0.05, n=4). For CD146, the mean fluorescent intensity was ~2-fold greater for multipotent MSCs than the parent culture (p<0.05, n=4). The use of single-cell derived MSC colonies and the isolation of the multipotent cells that correlates to more than 40% efficiency in colony formation, revealed the high expression of CD146 and NG2 in the desired MSCs.

The invention can be employed, for instance, to monitor MSC preparations in the clinic for consistent content of multipotent cells and to determine the variability in heterogeneity among different donors, with age and under different culture conditions. The method of this invention can used to identify other factors associated with MSC multipotency.

Using this invention makes it possible to exploit differential growth kinetics to enrich multipotent cells in a heterogeneous MSC preparation during ex vivo amplification for clinical use by using the markers NG2 and CD146. The ease of identification of MSCs with multipotency and efficient colony formation, and further culturing of the isolated MSCs with high expression of CD146 and NG2, can provide a source of MSCs for therapy and research.

What we claim is:
1. A method of identifying human multipotent mesenchymal stem cells capable of high proliferation that have a cell doubling time of 30-hours or less, comprising the steps of
   collecting mesenchymal stem cells;
   measuring the expression of NG2; and
   isolating the mesenchymal stem cells having a colony forming efficiency of greater than 40% with high expression of NG2 by selecting the mesenchymal stem cells having high antibody binding capacity (ABC) of anti-NG2 antibodies of at least 100,000 molecules of anti-NG2 antibodies per mesenchymal stem cell.

2. The method of identifying human multipotent mesenchymal stem cells capable of high proliferation of claim 1 comprising the additional step of:
   minimizing the senescent cells in the mesenchymal stem cells selected in claim 1 by adding a marker for senescent cells to the mesenchymal stem cells;
   measuring the marker indicating senescent cells; and
   isolating the cells with high expression of NG2 and low indication of the marker for senescent cells.

3. The method of identifying human multipotent mesenchymal stem cells capable of high proliferation of claim 1 comprising the additional step of:
   minimizing lineage-committed cells in the mesenchymal stem cells selected in claim 1 by adding a marker for lineage-committed cells to the mesenchymal stem cells;
   measuring the marker indicating lineage-committed cells; and
   isolating the cells with high expression of NG2 and low indication of the marker for lineage-committed cells.

4. A method of identifying human multipotent mesenchymal stem cells capable of high proliferation that have a cell doubling time of 30 hours or less, comprising the steps of
   collecting mesenchymal stem cells;
   measuring the expression of CD146 and NG2; and
   isolating the mesenchymal stem cells having a colony forming efficiency of greater than 40% with high expression of CD146 and NG2 by selecting the mesenchymal stem cells having high antibody binding capacity (ABC) of anti-CD146 and anti-NG2 antibodies, wherein the selection criteria being the ABC values of at least 100,000 molecules of anti-NG2 antibodies and at least 200,000 molecules of anti-CD146 antibodies per mesenchymal stem cell.

5. The method of identifying human multipotent mesenchymal stem cells capable of high proliferation of claim 4 comprising the additional step of:
   minimizing the senescent cells in the mesenchymal stem cells selected in claim 4 by adding a marker for senescent cells to the mesenchymal stem cells;
   measuring the marker indicating senescent cells; and
   isolating the cells with high expression of CD146 and NG2 and low indication of the marker for senescent cells.

6. The method of identifying human multipotent mesenchymal stem cells capable of high proliferation of claim 4 comprising the additional step of:
   minimizing lineage-committed cells in the mesenchymal stem cells selected in claim 4 by adding a marker for lineage-committed cells to the mesenchymal stem cells;
   measuring the marker indicating lineage-committed cells; and
   isolating the cells with high expression of CD146 and NG2 and low indication of the marker for lineage-committed cells.

7. A method for identification and culture of human multipotent mesenchymal stem cells with high proliferation potential that have a cell doubling time of 30 hours or less, comprising the steps of:
   collecting mesenchymal stem cells from tissue;
   immunophenotyping the cells for high expression of NG2; and
   isolating the cells with high expression for NG2 by selecting the mesenchymal stem cells having high antibody binding capacity (ABC) of anti-NG2 antibodies of at least 100,000 molecules of anti-NG2 antibodies per mesenchymal stem cell.

8. The method for identification and culture of human multipotent mesenchymal stem cells with high proliferation potential of claim 7 comprising the additional step of:
   culturing the cells selected in claim 7.

9. The method for identification and culture of human multipotent mesenchymal stem cells with high proliferation potential of claim 8, comprising the additional step of:
   cryopreserving the cultured cells.

10. The method for identification and culture of human multipotent mesenchymal stem cells with high proliferation potential of claim 7 comprising the additional steps of
    culturing the cells selected in claim 7; and
    monitoring the presence of NG2.

11. The method for identification and culture of human multipotent mesenchymal stem cells with high proliferation potential of claim 7 comprising the additional steps of:
    culturing the cells selected in claim 7;
    monitoring the presence of NG2;
    isolating the cells with high expression of NG2; and
    further culturing the cells selected in the prior step.

12. A method for identification and culture of human multipotent mesenchymal stem cells with high proliferation potential that have a cell doubling time of 30 hours or less, comprising the steps of
    collecting mesenchymal stem cells from tissue;
    immunophenotyping the cells for CD146 and NG2; and
    isolating the cells with high expression of CD146 and NG2 by selecting the mesenchymal stem cells having high antibody binding capacity (ABC) of anti-CD146 and anti-NG2 antibodies, wherein the selection criteria being the ABC values of at least 100,000 molecules of anti-NG2 antibodies and at least 200,000 molecules of anti-CD146 antibodies per mesenchymal stem cell.

13. The method for identification and culture of human multipotent mesenchymal stem cells with high proliferation potential of claim 12 comprising the additional step of:
    culturing the cells selected in claim 12.

14. The method for identification and culture of human multipotent mesenchymal stem cells with high expression of CD146 and NG2 and with high proliferation potential of claim 13, comprising the additional step of:
    cryopreserving the cultured cells.

15. The method for identification and culture of human multipotent mesenchymal stem cells with high proliferation potential of claim 12 comprising the additional steps of:
    culturing the cells selected in claim 12; and
    monitoring the presence of CD146 and NG2.

16. The method for identification and culture of human multipotent mesenchymal stem cells with high proliferation potential of claim 12 comprising the additional steps of
    culturing the cells selected in claim 12;
    monitoring the presence of CD146 and NG2;
    isolating the cells with high expression of CD146 and NG2; and
    further culturing the cells selected in the prior step.

* * * * *